United States Patent [19]

Arai et al.

[11] Patent Number: 4,895,704

[45] Date of Patent: Jan. 23, 1990

[54] INTEGRAL MULTILAYER ANALYTICAL ELEMENT

[75] Inventors: Fuminori Arai; Takeshi Igarashi, both of Saitama, Japan

[73] Assignee: Fuji Photo Film Co., Ltd., Kanagawa, Japan

[21] Appl. No.: 117,355

[22] Filed: Oct. 27, 1987

Related U.S. Application Data

[63] Continuation of Ser. No. 854,346, Apr. 21, 1986, abandoned.

[30] Foreign Application Priority Data

Apr. 23, 1985 [JP] Japan .................. 60-853336

[51] Int. Cl.[4] ............................................ G01N 31/22
[52] U.S. Cl. ....................................... 422/57; 422/56; 435/805; 436/169; 436/170
[58] Field of Search ................... 422/57, 56; 436/169, 436/170; 435/805

[56] References Cited

U.S. PATENT DOCUMENTS

| | | | |
|---|---|---|---|
| 3,630,957 | 12/1971 | Rey et al. ........................ | 422/56 X |
| 3,992,158 | 11/1976 | Przybylowicz et al. ............. | 422/57 |
| 4,042,335 | 8/1977 | Clement ............................ | 422/58 |
| 4,312,834 | 1/1982 | Vogel et al. ....................... | 422/56 |
| 4,587,102 | 5/1986 | Nagatomo et al. ................. | 422/56 |

FOREIGN PATENT DOCUMENTS

| | | |
|---|---|---|
| 0162302 | 11/1975 | European Pat. Off. . |
| 0114403 | 8/1984 | European Pat. Off. . |
| 2191734 | 2/1974 | France . |
| 1440464 | 6/1976 | United Kingdom . |

*Primary Examiner*—Barry S. Richman
*Assistant Examiner*—Jill Johnston
*Attorney, Agent, or Firm*—Jules E. Goldberg

[57] ABSTRACT

An integral multilayer analytical element which comprises a water-impermeable light-transmissive support, a hydrophilic layer containing a water-absorptive hydrophilic polymer binder and a spreading layer superposed in this order, and contains at least one reagent capable of reacting with a component of a sample to produce a detectable species capable of detecting by light, which is characterized in that light-scattering particulates in an amount to make light transmittance to 10 to 2.5% are contained in the above hydrophilic layer and/or a layer located on the side of the support therefrom. This element may decrease the influence of a conventional reagent layer up to the extent being negligible without lowering the sensitivity. Precision of the measurement at a low concentration range is also high, and reproducibility of the meaurement is well. Manufacture of this element is easy.

15 Claims, No Drawings

INTEGRAL MULTILAYER ANALYTICAL ELEMENT

This is a continuation of application Ser. No. 854,346, filed Apr. 21, 1986, now abandoned.

BACKGROUND OF THE INVENTION

1. Field of the Invention

This invention relates to an improvement of a dry-type integral multilayer analytical element for analysis of a particular component in a liquid sample. More particularly, this invention relates to an integral multilayer analytical element useful for analysis of an aqueous liquid sample such as for a clinical test where a body fluid is employed as a sample.

2. Description of prior arts

Recently, as a dry-type analytical element, many integral multilayer analytical elements wherein a water-absorptive reagent layer and a porous spreading layer are provided on a light-transmissive support have been proposed. The reagent layer contains reagents for color-forming reaction and a hydrophilic polymer binder, and the porous spreading layer is located at the topmost layer. In such multilayer analytical elements, an aqueous liquid sample spotted on the spreading layer spreads in this layer, and it reaches the reagent layer. Then, it reacts with the reagents to produce a detectable species such as a colored substance. The object substance such as a particular component of a body fluid can be determined by measuring this detectable species.

As the means to measure the detectable species it is known that a porous light-reflecting layer is provided above the reagent layer (U.S. Pat. No. 3,992,158). In the case of this analytical element, light is irradiated from under the support, and the reflected light is measured. Precision of this method is raised because influence of the suspensoids such as blood cells which inhibit the measurement can be removed. As the light-reflecting layer, various blushed polymer layers are disclosed in the specification of the above patent. They include a microporous blushed polymer layer formed by the deposition of polycarbonate particulates, polyamide particulates, cellulose enter particulates, etc., such as microporous filter membrane "Millipore" or "Metricell" formed by blushed polymer of cellulose enter, and a microporous layers where particulates of titanium dioxide, barium sulfate, etc. are dispersed in a binder such as cellulose acetate, polyvinyl alcohol or gelatin.

On the other hand, it is also known that a radiation-blocking layer is provided under the reagent layer (U.S. Pat. No. 4,042,335). In the case of this analytical element, the detectable species produced in the reagent layer passes through this radiation-blocking layer, accumulates in the detection layer located thereunder. Light irradiated from under the support is blocked by the radiation-blocking layer. That is, it is intended that the transmittance at the wave length to be measured is made less than about 1.0% (optical density is larger than about 2.0.), and influence of the reagent layer on the measurement of the detectable species can be nullified. The material of the radiation-blocking layer can include a matrix containing particulates of an inorganic pigment such as carbon black, titanium dioxide, zinc oxide or barium sulfate dispersed therein and the blushed polymer layer in which the above inorganic pigment is added, can be utilized.

However, when the light-reflecting layer is provided above the reagent layer, influence of the reagent layer largely appears. On the other hand, in the case that the radiation-blocking layer is introduced, the sensitivity of the measurement is lowered because the amount of the detectable species passing through this layer remarkably decreases. Particularly, when a light-reflecting pigment such as titanium dioxide particulates is employed for the light-reflecting layer or the radiation blocking layer, it is necessary to increase its content in order to secure the light reflectance or the radiation-blocking. As a result, it becomes difficult to form the above layers uniformly, and the physical strength of the layers becomes weak because the content of the polymer binder in the layers lowers.

SUMMARY OF THE INVENTION

An object of the present invention is to provide an integral multilayer analytical element capable of removing the influence of a reagent layer without lowering the sensitivity.

Another object of the present invention is to provide an integral multilayer analytical element in which the layer containing particulates of a light-reflecting pigment in a high concentration is eliminated, and thereby facilitating its manufacture increasing its physical strength.

Still another object of the present invention is to provide an integral multilayer analytical element of which the number of layers is decreased and thereby facilitating its manufacture.

A further object of the present invention is to provide an integral multilayer analytical element having improved precision in measurements at a low concentration range by lowering its blank value.

A still further object of the present invention is to provide an integral multilayer analytical element capable of high precision measurements over a wide concentration range by lowering the blank value.

The present invention provides an integral multilayer analytical element which has achieved these objects, and based upon the knowledge that, when a small amount of light-scattering particulates such as titanium dioxide is added to the layer where a detectable species is accumulated or a layer located on the side of the support therefrom, the detectable species can be determined in a high sensitivity and a high precision.

Thus, the integral multilayer analytical element of the present invention comprises a water-impermeable light-transmissive support, a hydrophilic layer containing a water-absorptive hydrophilic polymer binder and a spreading layer superposed in this order, and containing at least one reagent capable of reacting with a component of a sample to produce a detectable species capable of detecting by light, which is characterized in that light-scattering particulates in an amount which makes light transmittance to 10-2.5% are added to the hydrophilic layer and/or a layer located on the side of the support therefrom.

DETAILED DESCRIPTION OF THE INVENTION

The subject to be measured is not limited, and includes various body fluid components such as cholesterol, uric acid, creatinine and enzymes, ammonia, saccharides such as glucose, and proteins. The sample containing such a subject is an aqueous liquid, and includes various body fluids, such as a blood sample including whole blood, blood plasma and blood serum, lymph, saliva, cerebrospinal fluid, vaginal fluid and urine, water to drink, river water, factory waste water, and alcoholic liquors.

As the water-impermeable light-transmissive support, a known support employed in an usual multilayer analytical element may be employed. Such a support is a sheet or a laminate having a thickness in the range from about 50 μm to about 1 mm, preferably from about 80 μm to about 0.3 mm and being clear in the range from near-ultraviolet to near infrared regions. Such a sheet or a laminate may be made from a polyester (for example, polyethylene terephthalate or poly-carbonate of bisphenol A), a cellulose ester (for example, cellulose diacetate, cellulose triacetate or cellulose acetate propionate), or polystyrene. A known undercoating layer or a known adhesive layer such as disclosed in the foregoing patent specifications may be provided on the surface of the support in order to secure the adhesion of the support to the hydrophilic layer, etc.

The hydrophilic layer is the layer to accumulate the detectable species produced by the reaction with a reagent, and consists of a hydrophilic polymer binder alone or together with other components such as reagents and additives. The hydrophilic layer may also function as a water absorption layer which absorbs water to swell and which receives and accumulates the detectable species, and as a registration layer which contains a mordant having negative charge or positive charge capable of immobilizing the detectable species and which absorbs water to swell. Examples of the hydrophilic polymer binder usable for the hydrophilic layer are gelatin including acid treated gelatin and deionized gelatin, gelatin delivatives such as phthalated gelatin and hydroxyalkyl acrylate grafted gelatin, agarose, pulluran, pullulan derivatives, polyacrylamide, polyvinyl alcohol and polyvinyl pyrrolidone. They are disclosed in Japanese Patent KOKAI No. 59-171864 and EP 0,142,849 A. Thickness of the hydrophilic layer in dry state is usually about 2 μm to about 100 μm, preferably about 3 μm to about 50 μm, particularly preferable about 5 μm to about 30 μm. It is preferable that the hydrophilic layer is substantially transparent. This hydrophilic layer may contain the light-scattering particulates described later, and in addition, a part of or whole reagents, a pH buffer composition, a macromolecular pH buffer, a base polymer, an acid polymer, a macromolecular mordant, etc., to be known may also be contained in this layer.

A reagent layer may be provided independently. As this reagent layer, the layer wherein a part of or whole reagents are uniformly dispersed into a hydrophilic polymer binder such as gelatin, polyvinyl alcohol or polyacrylamide disclosed in the specifications of U.S. Pat. No. 3,992,158, U.S. Pat. No. 4,089,747 and U.S. Pat. No. 4,042,335 and the layer wherein hydrophobic particulates containing reagents are dispersed into a hydrophilic polymer binder disclosed in U.S. Pat. No. 4,356,149 may be utilized. The reagent layer may contain a pH buffer composition, a macromolecular pH buffer, a base polymer, an acid polymer, a macromolecular mordant, etc., to be known.

The spreading layer spreads a liquid sample. Various non-fibrous isotropically porous spreading layers, such as a membrane filter (blushed polymer layer) disclosed in U.S. Pat. No. 3,992,158, a continuous microspaces-containing porous layer where polymer particulates, glass particulates or diatomaceous earth are dispersed in a hydrophilic polymer binder, a continuous microspaces-containing porous layer where polymer particulates, glass particulates, etc. are joined so as to contact with each other at a point by using a polymer adhesive which does not swell in water (three-dimensional lattice structure layer) disclosed in U.S. Pat. No. 4,258,001, and various fibrous porous spreading layers, such as a spreading layer of woven fabric disclosed in U.S. Pat. No. 4,292,272 a spreading layer of knitted fabric disclosed in EP 0,162,302 A and a spreading layer comprising a paper containing a fibrous pulp of an organic polymer disclosed in Japanese Patent KOKAI No. 57-148250 may be utilized.

Various layers disclosed in the specifications of the foregoing patents may be introduced into the multilayer element of the invention. Such layers include a filter layer, a semipermeable membrane layer, a barrier layer, a diffusionhindering layer (migration-inhibiting layer) and a layer having two or more of the functions mentioned above.

The hydrophilic layer and the substantially nonporous reagent layer may be provided on the foregoing water-impermeable light-transmissive support by a known application method. A microporous reagent layer may be provided according to the method disclosed in the specifications of EP 0,114,403 A and EP 0,115,873 A. The reagent layer should be located higher than the hydrophilic layer.

The reagent(s) reacts with a component of a sample to produce a detectable species capable of detecting by light. The light may be visible light, ultraviolet light or infrared light. The detectable species includes a colored substance, a fluorescent material, an ultraviolet absorbing material, an infrared absorbing material, suspended matter, emulsified matter and a material to vary or decrease one or more of these materials. Examples of the reagent include various reagent compositions containing enzyme disclosed in the foregoing patent specifications and other known analytical reagents and clinical reagents for diagnosis.

The reagent may be contained in the spreading layer, the hydrophilic layer and/or the reagent layer which is introduced separately. When the reagent is unstable and it is denatured by contact with air, this reagent is preferably added to an inner layer such as the hydrophilic layer or the reagent layer. When two or more reagents are employed, all reagents may be added to one layer or two or more layers. In the case that the reagent is contained in the spreading layer, it is preferable that the spreading layer is first laminated on the hydrophilic layer, and then the reagent solution is applied thereon as described in the specifications of Japanese Patent KOKAI No. 59-171864, EP 0,162,301 A and EP 0,162,302 A.

The integral multilayer analytical element of the invention is characterized in that a particular amount of the light-scattering particulates is dispersed into the hydrophilic layer where the detectable species is accumulated and/or a layer located on the side of the support therefrom.

Suitable mean particle size of the light-scattering particulates is in the range of about 0.1 μm to about 2 μm, preferably about 0.2 μm to about 1 μm. Examples of the light-scattering particulates are titanium dioxide particulates such as rutile, anatase and brookite microcrystalline particulates having a particle size of about 0.1 μm to about 1.2 μm, barium sulfate particulates and aluminum particulates and microflakes. Among, them, titanium dioxide particulates and barium sulfate particulates are preferable.

The medium where the light-scattering particulates are dispersed should be light-transmissive. For example, the hydrophilic polymer binder mentioned previously and other weakly hydrophilic materials such as regenerated cellulose and cellulose acetate may be employed. Among these, gelatin, its derivative and polyacrylamide are preferable. A known hardening agent (cross-linking agent) may be added to gelatin or its derivative. A hydrophobic medium such as diacetyl cellulose may also be employed. The light-scattering particulates may be dispersed in the support. The layer containing the light-scattering particulates may be located on the reverse side of the support. The amount of the light-scattering particulates is to make the transmittance at the wave length used for measuring detectable species to about 10% to about 2.5%, preferably about 8% to about 3%, more preferably about 6% to about 3%. The light-scattering particulates may be added to two or more layers, and in this case, the above amount is the total amount contained in the layers. Thickness of the layer containing the light-scattering particulates is in the range of about 2 μm to about 100 μm, usually about 3 μm to about 50 μm, preferably about 5 μm to about 30 μm, in dry state. When the light-scattering particulates are added to two or more layers, the above thickness is the total thickness summed up the layers containing the light-scattering particulates. The layer containing the light-scattering particulates is translucent. When white particulates such as titanium dioxide and barium sulfate are employed, appearance of the layer containing such light-scattering particulates is milk white and translucent.

The integral multilayer analytical element of the invention is preferably cut into square or circular pieces having a side or diameter of about 15 mm to about 30 mm, and put in a silde frame disclosed in Japanese Patent KOKAI No. 57-63452, U.S. Pat. No. 4,169,751, U.S. Pat. No. 4,387,990, PCT application WO 83/00391, etc. to use.

The measurement is carried out, for example, according to the manner disclosed in the specifications of the foregoing patents. About 5 μl to about 30 μl, preferably about 8 μl to about 15 μl of an aqueous sample is spotted on the spreading layer, and incubated at a definite temperature in the range of about 20° C. to about 45° C. for a prescribed time, if necessary. Thereafter, a detectable variation such as color change or coloring in the multilayer analytical element is measured from the side of the support through reflection photometry, and the subject component in the sample is determined by the principle of colorimetry.

In the multilayer analytical element of the present invention, the influence of a conventional reagent layer decreases and becomes negligible without lowering the sensitivity. The blank value of this element is low, and precision of the measurement at a low concentration range is also high. As a result of these, the effect comparative to the introduction of a registration layer is obtained with respect to the influence of contaminates. In the multilayer analytical element of the invention, a reflecting layer and a light-shielding layer are not necessary, and accordingly, at least one layer can be eliminated. Uniform application of the layer containing the light-scattering particulates is easy because of its low concentration. As a result of these factors manufacture of the element of the invention is facilitated. In the measurement using the multilayer analytical element of the invention, the base line is stable, and reproducibility is high.

The following examples are given to illustrate the present invention in more detail.

EXAMPLE 1

A colorless transparent polyethylene terephthalate (PET) film of which the thikness was 180 μm and on which gelatin undercoating was provided was employed as the support. A hydrophilic layer (water absorption layer) having the following composition where titanium dioxide particulates were dispersed was applied on the above support so that its dry thickness became about 20 μm, and dried. Light transmittance at the wave length of 540 nm and its vicinity of the dry hydrophilic layer was 3.1%.

| | |
|---|---|
| Gelatin | 24 g |
| Polyoxyethylene nonyl phenyl ether (Nonionic surfactant, Containing 10 hydroxyethylene units (average)) | 1.2 g |
| Rutile type titanium dioxide particulates (Particle size; 0.20–0.35 μm) | 0.4 g |
| Bis (vinylsulfonyl methyl) ether | 0.3 g |

The hydrophilic layer was dampened with water. A PET tricot fabric cloth (knitted from 50 deniers PET spun yarn by 50 gauges, being about 300 μm in thickness) treated with glow discharge was pressed to laminate thereon as the spreading layer, and then dried.

Subsequently, an aqueous solution of a reagent composition for the detection of cholesterol having the following composition was applied on the spreading layer, and dried to prepare an integral multilayer analytical element for the determination of cholesterol.

| | |
|---|---|
| Octylphenoxypolyethoxyethanol (Nonionic sarfactant, hydroxyethylene units; 9–10) | 0.7 g/m$^2$ |
| Sodium 2-hydroxy-3,5-dichlorobenzene sulfonate | 1.8 g/m$^2$ |
| 4-aminoantipyrine | 0.3 g/m$^2$ |
| Dimedone [126-81-8] | 0.7 g/m$^2$ |
| Cholesterol oxidase | 3500 IU/m$^2$ |
| Cholesterol esterase | 20000 IU/m$^2$ |
| Peroxidase | 29000 IU/m$^2$ |

The element thus obtained was cut into square pieces of 15 mm×15 mm, and each piece was placed in the plastic mount disclosed in Japanese Patent KOKAI No. 57-63452 to form a chemical-analytical slide for cholesterol determination.

As a comparison, another chemical-analytical slide for cholesterol determination was prepared in the same manner as above except that titanium dioxide particulates were not added to the hydrophilic layer.

Influence of hemolysate (hemoglobin dissolved in blood plasma or serum) on the measurement of choresterol was examined by using the above two kinds of the slides. Hemoglobin of which the amount was described in Table 1 was added to control serum "Versatol-P" (Warner-Lambert) to prepare sample solutions containing hemoglobin. Each 8 μl of the sample solution was spotted on the spreading layer of each slide, and incubated at 37° C. for 6 minutes. Reflection optical density was measured by using a light having a central wave length of 540 nm from the PET film side, and cholesterol content was determined by reference to a calibration curve prepared previously. The results are shown in Table 1.

TABLE 1

| Hemoglobin Content (mg/dl) | 0 | 102 | 223 | 350 |
|---|---|---|---|---|
| Cholesterol Content (mg/dl) | | | | |
| Obtained by Example 1 Slide | 183 | 184 | 182 | 179 |
| Obtained by its Comparative Slide | 183 | 187 | 192 | 199 |

The above results indicate that the positive error caused by hemoglobin in the sample serum is removed in the element of the invention.

EXAMPLE 2

A colorless transparent PET film of which the thickness was 180 μm and on which gelatin undercoating was provided was employed as the support.

A hydrophilic layer (registration layer) having the following composition where titanium dioxide particulates were dispersed was applied on the above support so that its dry thickness became about 20 μm, and dried. Light transmittance at the wave length of 420 nm and its vicinity of the dry hydrophilic layer was 5.8%.

| Styrene-(N—vinylbenzyl-N, N—dimethly ammonium chloride)-divinylbenzene trimer copolymer | 19 g |
|---|---|
| Gelatin | 50 g |
| Rutile type titanium dioxide particulates (Particle size; 0.20-0.35 μm) | 0.8 g |
| Polyoxyethylene nonyl phenyl ether (Hydroxyethylene units; 10 (average)) | 1 g |

The hydrophilic layer was dampened with water. A PET tricot fabric cloth (knitted from 50 deniers PET union yarn, being about 250 μm in thickness) treated with glow discharge was pressed to laminate thereon as the spreading layer, and then dried.

Subsequently, an aqueous solution of the reagent composition for the detection of bilirubin having the following composition was applied on the spreading layer, and dried to prepare an integral multilayer analytical element for the determination of bilirubin.

| Diphylline [20267-87-2] | 20 g/m² |
|---|---|
| Caffeine | 10 g/m² |
| Polyoxyethylene nonyl phenyl ether (Hydroxyethylene units; 10 (average)) | 0.5 g/m² |

The element thus obtained was cut into square pieces, and each piece was placed in the plastic mount to form a chemical-analytical slide for bilirubin determination according to the same manner as Example 1.

As a comparison, another chemical-analytical slide for bilirubin determination was prepared in the same manner as above except that titanium dioxide particulates were not added to the hydrophilic layer.

Influence of hemoglobin dissolved in blood serum on the measurement of bilirubin was examined by using the above two kinds of the slides. Hemoglobin of which the amount was described in Table 2 was added to control serum "Monitorol II" (Dade) containing 5.2 mg/dl of bilirubin. Each 10 μl of the sample solution was spotted on the spreading layer of each slide, and incubated at 37° C. for 6 minutes. Reflection optical density was measured by using a light having a central wave length of 420 nm from the support (PET film) side, and bilirubin content was determined by reference to a calibration curve prepared previously. The results are shown in Table 2.

TABLE 2

| Hemoglobin Content (mg/dl) | 0 | 21 | 70 | 182 |
|---|---|---|---|---|
| Bilirubin Content (mg/dl) | | | | |
| Obtained by Example 2 Slide | 5.2 | 5.1 | 5.2 | 5.3 |
| Obtained by its Comparative Slide | 5.1 | 5.3 | 5.7 | 6.2 |

The above results indicate that the positive error caused by hemoglobin in the sample serum is removed in the element of the invention.

EXAMPLE 3

In order to confirm the reproducibility of the element of the invention, the following experiments were carried out. Each 10 μl of the control serum "Monitorol II" containing 5.2 mg/dl of bilirubin was spotted to each of the chemical-analytical slide of Examples 2 and its comparative slide described in Example 2, and incubated at 37° C. for 6 minutes. The bilirubin content was determined in the same manner as Example 2. This determination operation was repeated 7 times. The results are shown in Table 3.

TABLE 3

| | 1 | 2 | 3 | 4 | 5 | 6 | 7 |
|---|---|---|---|---|---|---|---|
| Example 2 Slide (mg/dl) | 5.2 | 5.1 | 5.2 | 5.1 | 5.2 | 5.2 | 5.1 |
| Its Comparative Slide (mg/dl) | 5.1 | 5.2 | 5.0 | 5.3 | 5.1 | 5.4 | 5.0 |

| | Standard Deviation (SD) | SD ÷ mean value × 100 |
|---|---|---|
| Example 2 Slide | 0.053 | 1.0% |
| Its Comparative Slide | 0.151 | 2.9% |

The above results indicate that the reproducibility of the element of the invention is good.

EXAMPLE 4

A colorless transparent PET film of which the thickness was 185 μm and on which gelatin undercoating was provided was employed as the support. A hydrophilic layer (reagent layer) having the following composition where titanium dioxide particulates were dispersed was applied on the above support so that its dry thickness became about 15 μm, and dried. Light transmittance at the wave length of 500 nm and its vicinity of the dry hydrophilic layer was 3.3%.

| Glucose oxidase | 10000 IU |
|---|---|
| Peroxidase | 25000 IU |
| 1,7-dihydroxynaphthalene | 5 g |
| 4-aminoantipyrine | 5 g |
| Deionized gelatin | 200 g |
| Polyoxyethylene nonyl phenyl ether (Hydroxyethylene units; 10 (average)) | 2 g |
| Rutile type titanium dioxide particulates (Particle size: 0.20-0.35 μm) | 3 g |

4 g of deionized gelatin and 0.2 g of polyoxyethylene nonyl phenyl ether (hydroxyethylene units; 10 (average)) were dissolved in 100 ml of water to produce an adhesive layer solution. This solution was applied on the hydrophilic layer to form an adhesive layer having a dry thickness of 4 μm.

The adhesive layer was dampened with water. A cotton broad-cloth (made of No. 100 count cotton yarn, about 200 μm in thickness) was pressed to laminate thereon as the spreading layer, and dried to prepare an integral multilayer analytical element for the determination of glucose. This element was cut into square pieces, and each piece was placed in the plastic mount to form a chemical-analytical slide for glucose determination according to the same manner as Example 1.

As a comparison, another chemical-analytical slide for glucose determination was prepared in the same manner as above except that titanium dioxide particulates were not added to the hydrophilic layer.

Measurements of glucose content were carried out as follows. Human blood was drawn with heparin, and centrifuged to obtain human blood plasma containing 98 mg/dl of glucose as a sample solution. Each 10 μl of the sample solution was spotted on the spreading layer of each slide, and incubated at 37° C. for 6 minutes. Reflection optical density was measured by using a light having a central wave length of 500 nm from the PET film side, and glucose content was determined by reference to a calibration curve prepared previously. The same measurements were repeated 20 times in order to examine reproducibility. The results are shown in Table 4.

TABLE 4

|  | 1 | 2 | 3 | 4 | 5 | 6 | 7 | 8 | 9 | 10 |
|---|---|---|---|---|---|---|---|---|---|---|
| Example 4 Slide | 98 | 98 | 98 | 96 | 98 | 98 | 99 | 99 | 98 | 98 |
| Comparative Slide | 95 | 99 | 90 | 96 | 98 | 96 | 99 | 102 | 96 | 96 |
|  | 11 | 12 | 13 | 14 | 15 | 16 | 17 | 18 | 19 | 20 |
| Example 4 Slide | 98 | 95 | 99 | 98 | 97 | 98 | 99 | 98 | 99 | 99 |
| Comparative Slide | 95 | 94 | 98 | 103 | 97 | 99 | 93 | 102 | 97 | 92 |

|  | Mean Value (x) | Standard Deviation (SD) | SD/x × 100 |
|---|---|---|---|
| Example 4 Slide | 98 mg/dl | 1.025 | 1.0% |
| Comparative Slide | 96.9 mg/dl | 3.329 | 3.4% |

The above results indicate that in the case of the element of the invention, dispersion of the measured values was small and the reproducibility was well.

EXAMPLE 5

Human blood was drawn with sodium fluoride, and centrifuged to obtain human blood plasmas. Four hemolyzed plasma samples (Nos. 1-4) were selected, and influence of homoglobin content upon the measurement of glucose concentration was examined by using the slide of Example 4 and its comparative slide.

Glucose concentrations of the four samples were determined by hexokinase method besides the above slides, and their hemoglobin contents were determined by cyanomethemoglobin method. The results are shown in Table 5.

TABLE 5

|  |  | 1 | 2 | 3 | 4 |
|---|---|---|---|---|---|
|  | Hemoglobin | 50 mg/dl | 125 | 192 | 300 |
|  | Y | 99 mg/dl | 123 | 86 | 88 |
| Example 4 | X | 98 mg/dl | 125 | 89 | 92 |
| Slide | X/Y | 0.99 | 1.02 | 1.03 | 1.05 |
| Comparative | X | 101 mg/dl | 137 | 107 | 124 |
| Slide | X/Y | 1.02 | 1.11 | 1.24 | 1.41 |

X: Glucose concentration measured by the slide
Y: Glucose concentration measured by hexokinase method The above results indicate that positive error caused by hemoglobin is depressed in a wide range of hemoglobin content in the element of the invention.

EXAMPLE 6

Reproducibility of the element of the invention was measured again by using the slide of Example 4.

As a comparative slide, the following one was used. A reagent layer being 15 μm in dry thickness and having the same composition as Example 4 except that titanium dioxide particulates were not added was provided on the PET film in the same manner as Example 4. 8 g of titanium dioxide particulates (Rutile type, particle size; 0.20-0.35 μm) was added to an aqueous gelatin solution containing 1 g of deionized gelatin, and mixed well. This suspension was applied on the above reagent layer so that its dry thickness became 10 μm, and dried to form a light-shielding layer. Light transmittance at the wave length of 500 nm and its vicinity of the light-shielding layer was 1.7%. On the light-shielding layer, the same adhesive layer and spreading layer as Example 4 were provided in the same manner as Example 4. The comparative element thus obtained was cut into square pieces, and each piece was placed in the plastic mount to form a chemical-analytical slide for glucose determination in the same manner as Example 4.

Human blood was drawn with heparin, and centrifuged to obtain three human plasma samples containing each 98 mg/dl, 326 mg/dl and 565 mg/dl of glucose. Using these samples and the slides prepared in Example 4 and the above comparative slides containing a light-shielding layer, 20 times determinations of glucose concentration per each sample were repeated. The results are shown in Table 6.

TABLE 6

| Human plasma sample 1 Containing 98 mg/dl of Glucose | | | | | | | | | | |
|---|---|---|---|---|---|---|---|---|---|---|
|  | 1 | 2 | 3 | 4 | 5 | 6 | 7 | 8 | 9 | 10 |
| Example 4 Slide | 98 | 98 | 98 | 96 | 98 | 98 | 99 | 99 | 98 | 98 |
| Comparative Slide | 99 | 100 | 99 | 98 | 97 | 99 | 99 | 100 | 98 | 97 |
|  | 11 | 12 | 13 | 14 | 15 | 16 | 17 | 18 | 19 | 20 |
| Example 4 Slide | 98 | 95 | 99 | 98 | 97 | 98 | 99 | 98 | 99 | 99 |
| Comparative Slide | 98 | 99 | 100 | 98 | 99 | 98 | 98 | 99 | 99 | 99 |

|  | Mean Value (x) | Standard Deviation (SD) | SD/x × 100 (%) |
|---|---|---|---|
| Example 4 Slide | 98.0 | 1.03 | 1.05 |
| Comparative Slide | 98.7 | 0.87 | 0.88 |

| Human Plasma Sample 2 Containing 326 mg/dl of Glucose | | | | | | | | | | |
|---|---|---|---|---|---|---|---|---|---|---|
|  | 1 | 2 | 3 | 4 | 5 | 6 | 7 | 8 | 9 | 10 |
| Example 4 Slide | 325 | 328 | 324 | 325 | 326 | 324 | 328 | 327 | 325 | 325 |
| Comparative Slide | 319 | 325 | 318 | 329 | 331 | 330 | 321 | 329 | 319 | 317 |

TABLE 6-continued

|  | 11 | 12 | 13 | 14 | 15 | 16 | 17 | 18 | 19 | 20 |
|---|---|---|---|---|---|---|---|---|---|---|
| Example 4 Slide | 326 | 327 | 328 | 324 | 325 | 324 | 328 | 325 | 325 | 326 |
| Comparative Slide | 328 | 326 | 314 | 331 | 319 | 317 | 329 | 334 | 327 | 339 |

|  | Mean Value (x) | Standard Deviation (SD) | SD/x̄ × 100 (%) |
|---|---|---|---|
| Example 4 Slide | 325.8 | 1.45 | 0.45 |
| Comparative Slide | 325.1 | 6.72 | 2.07 |

Human Plasma Sample 3 Containing 565 mg/dl of Glucose

|  | 1 | 2 | 3 | 4 | 5 | 6 | 7 | 8 | 9 | 10 |
|---|---|---|---|---|---|---|---|---|---|---|
| Example 4 Slide | 563 | 565 | 570 | 570 | 565 | 564 | 561 | 570 | 565 | 572 |
| Comparative Slide | 553 | 541 | 563 | 569 | 578 | 542 | 550 | 572 | 561 | 542 |

|  | 11 | 12 | 13 | 14 | 15 | 16 | 17 | 18 | 19 | 20 |
|---|---|---|---|---|---|---|---|---|---|---|
| Example 4 Slide | 560 | 562 | 563 | 570 | 572 | 565 | 560 | 560 | 563 | 572 |
| Comparative Slide | 549 | 569 | 562 | 574 | 572 | 569 | 549 | 559 | 579 | 549 |

|  | Mean Value (x) | Standard Deviation (SD) | SD/x̄ × 100 (%) |
|---|---|---|---|
| Example 4 Slide | 566.2 | 4.49 | 0.79 |
| Comparative Slide | 560.1 | 12.45 | 2.22 |

The above results indicate that reproducibility of the element of the invention is superior in a wide range of glucose concentration in a plasma sample.

We claim:

1. In an integral multilayer analytical element which comprises a water-impermeable light-transmissive support, a hydrophilic layer containing a water-absorptive hydrophilic polymer binder and a spreading layer superposed in this order, and containing at least one reagent capable of reacting with a component of a sample to produce a detectable species capable of detection by light, the improvement which comprises said hydrophilic layer containing light-scattering particulates in an amount to make light transmittance in the range from 10 to 2.5%.

2. In an integral multilayer analytical element which comprises a water-impermeable light-transmissive support, a hydrophilic layer containing a water-absorptive hydrophilic polymer binder and a spreading layer superposed in this order, and containing at least one reagent capable of reacting with a component of a sample to produce a detectable species capable of detection by light, the improvement which comprises an additional layer on the same side of the support as said hydrophilic layer; said additional layer containing light-scattering particulates in an amount to make light transmittance in the range from 10 to 2.5%.

3. The integral multilayer analytical element of claim 1, wherein said reagent is contained in said spreading layer.

4. The integral multilayer analytical element of claim 1 or 2, wherein mean particle size of said light-scattering particulates is in the range of 0.1 μm to 2 μm.

5. The integral multilayer analytical element of claim 4, wherein said light-scattering particulates are titanium dioxide particulates or barium sulfate particulates.

6. The integral multilayer analytical element of claim 1 or 2, wherein said light-scattering particulates are contained in said hydrophilic layer.

7. The integral multilayer analytical element of claim 4 or 6, wherein said reagent is contained in said hydrophilic layer.

8. The integral multilayer analytical element of claim 7 wherein a mordant is contained in said hydrophilic layer.

9. The integral multilayer analytical element of claim 1 or 2, wherein said support is selected from the group consisting of polyethylene terephthalate, polycarbonate, a cellulose ester and polystyrene.

10. The integral multilayer analytical element of claim 1 or 2, wherein said hydrophilic polymer binder is selected from the group consisting of gelatin, gelatin derivatives, agarose, pullulan, pullulan derivatives, polyacrylamide, polyvinyl alcohol and polyvinyl pyrrolidone.

11. The integral multilayer analytical element of claim 1 or 2, wherein said spreading layer is selected from the group consisting of a membrane filter, a continuous microspaces-containing porous layer, a spreading layer of woven fabric, a spreading layer of knitted fabric and a spreading layer comprising a paper containing a fibrous pulp of an organic polymer.

12. The integral multilayer analytical element of claim 1 or 2, wherein said hydrophilic layer contains a water-absorption layer.

13. The analytical element of claim 1 or 2 wherein the hydrophilic layer contains a registration layer.

14. In a method for the detection of a blood component wherein a blood sample is placed on an integral multilayer analytical element and analyzed the improvement wherein said analytical element comprises a superposed in this order, a water-permeable light-transmissive support, a hydrophilic layer containing a water-absorptive hydrophilic polymer binder, and a spreading layer, and which further contains at least one reagent capable of reacting with a component of the sample to produce a detectable species capable of detection by light, and wherein said hydrophilic layer contains light scattering particulates in an amount to make the light transmittance in the range from 10 to 2.5%.

15. The method of claim 14, wherein said component is cholesterol, uric acid, creatinine, enzymes, ammonia, saccharides or proteins.

* * * * *